United States Patent [19]
Russell et al.

[11] Patent Number: 4,941,479
[45] Date of Patent: Jul. 17, 1990

[54] SURGICAL WRAP WITH ARM SPLINT

[75] Inventors: John P. Russell, Centerpoint; Sam Miller, Birmingham; Terry Carroll, Dora, all of Ala.

[73] Assignee: Infection Control Products, Inc., Gardendale, Ala.

[21] Appl. No.: 402,914

[22] Filed: Sep. 5, 1989

[51] Int. Cl.$^5$ .............................................. A61N 1/00
[52] U.S. Cl. .................................... 128/877; 128/854; 128/855; 128/DIG. 6
[58] Field of Search ............. 128/877, 878, 165, 80 R, 128/82, 84 C, 85, 87 R, 90, DIG. 6, 869-874, 157, 849, 854-856

[56] References Cited
U.S. PATENT DOCUMENTS

| | | | |
|---|---|---|---|
| 2,409,195 | 6/1946 | Crawford | 128/87 |
| 2,606,554 | 8/1952 | Simon | 128/165 |
| 2,763,264 | 9/1956 | McInnerny | 128/877 |
| 2,948,278 | 8/1960 | Topa | 128/873 |
| 3,059,636 | 10/1962 | Schwartz | 128/133 |
| 3,125,093 | 3/1964 | Hutchins | 128/157 |
| 3,279,459 | 10/1966 | Schenker | 128/165 |
| 3,513,842 | 5/1970 | Keenan et al. | 128/82 |
| 3,752,147 | 8/1973 | Castro et al. | 128/87 R X |
| 3,896,799 | 7/1975 | Seeley | 128/87 R |
| 4,043,330 | 8/1977 | Bansal | 128/133 |
| 4,047,250 | 9/1977 | Norman | 128/165 X |
| 4,215,687 | 8/1980 | Shaw | 128/165 X |
| 4,369,774 | 1/1983 | Robbins | 128/133 |
| 4,470,410 | 9/1984 | Elliot | 128/133 |
| 4,615,339 | 10/1986 | Siwek | 128/133 |
| 4,662,366 | 5/1987 | Tari | 128/134 |
| 4,716,892 | 1/1988 | Brunswick | 128/87 R X |

FOREIGN PATENT DOCUMENTS

| | | | |
|---|---|---|---|
| 162610 | 11/1985 | European Pat. Off. | 128/165 |
| 245897 | 1/1926 | United Kingdom | 128/165 |
| 86/05971 | 10/1986 | World Int. Prop. O. | 128/82 |

Primary Examiner—Robert A. Hafer
Assistant Examiner—Kevin G. Rooney
Attorney, Agent, or Firm—George A. Bode

[57] ABSTRACT

A protecting and restraining apparatus for use in applying an intravenous or catheter system to an extremity of the body for substantially immobilizing the extremity while permitting continued intravenous or catheter system operation comprising: an elongated flexible sheet member adapted to be wrapped about and encompass the arm, the sheet member further comprising a main base portion and a plurality of straps integrally formed with and transversely depending from the main base portion at a marginal longitudinal edge of the main base portion, each of the straps being connected to its adjacent straps at selective points along confronting marginal transverse edges of the adjacent straps; a flexible sleeve member being pivotally attached to a first surface of the sheet member coextensively along one marginal longitudinal edge of the sleeve member so as to allow pivoting of the sleeve member toward and away from the first surface of the sheet member, the sleeve being adapted to accept and retain a stiffener member by being open at at least one end; and, a fastener positioned near the longitudinal marginal edge of the straps for adhering to the second surface of the sheet member, thereby allowing selective tightening of the apparatus.

21 Claims, 7 Drawing Sheets

SURGICAL WRAP WITH ARM SPLINT

BACKGROUND OF THE INVENTION

1. Field of the Invention

The present invention relates to a supporting and restraining apparatus for use in applying an intravenous or catheter system to an extremity of the body for substantially stabilizing the extremity while permitting continuous intravenous or catheter system operation. More particularly, the apparatus of the present invention is an arm splint or board and surgical wrap for supporting and restraining the arm during intravenous infusions and other medical applications.

2. General Background

In a life threatening situation a paramedic's most valuable commodity is his time. The less time that it takes to remove his patient from the emergency situs to the medical facility, the better the chances of survival for the patient. Almost as important as time is convenience. If the paramedic can handle a procedure alone that frees his partner to attend to other critical matters that must be considered at the scene of an accident or any other medical emergency.

The traditional method requires four (4) separate items to complete an intravenous ("IV") infusion and support and restrain the arm. A paramedic needs gauze pads, an IV arm board or splint, elastic bandaging and tape. After removing these four (4) items from his storage bag, the paramedic places the pads under the patient's arm to absorb any blood that might flow when the IV is commenced; then, after the IV infusion is completed, he lifts the arm and puts the IV board under the arm to keep it straight; he then secures the board to the arm by wrapping them together with the elastic bandaging; and, finally, secures the end of the bandaging with tape. This traditional method is time consuming because it involves so many different items and can be messy and inconvenient for just one person. Even the most careful paramedic will frequently get blood on clothing, furniture or carpeting while inserting the IV. This is because the conventional 4×4 pads are small and do not always catch all of the blood. In addition, the process of wrapping the elastic bandage around the arm and the board is awkward; it is not uncommon for the board to slide away or for the roll of bandage to be dropped so that it unravels. When the bandage unravels, the paramedic usually either throws it away or rewinds the roll; thus, the process is much easier if performed by two (2) people. It is easy to understand why paramedics are frustrated by the prior art with its cumbersome process for completing an IV line at the scene of an emergency.

Some prior art patents and devices have developed using such padding and wrapping features.

U.S Pat. No. 4,043,330 issued to S. K. Bansal and U.S. Pat. No. 3,059,636 issued to J. Schwartz disclose padded boards with separate adhesive wrappings. U.S. Pat. No. 4,662,366 issued to L. G. Tari discloses a flexible sheet adapted to be wrapped around the patient and separate adhesive straps for holding the wrapping in place.

U.S. Pat. No. 3,896,799 issued to W. C. Seeley discloses an arm board for use in connection with intravenous feeding that is padded and has a tear-off portion suitable for strapping the arm to the board. U.S. Pat. No. 2,409,195 issued to W. J. Crawford discloses a surgical splint having a base panel and foldable side panels which can be separated along a score line for wrapping a device to the arm.

It is an object of the present invention to save time in completing the medical procedure of intravenous catheterization, particularly at the scene of a medical emergency.

It is a further object of the present invention to provide a single device that replaces the conventional four (4) separate items that are normally required for a paramedic to immobilize an arm and apply intravenous catheterization.

SUMMARY OF THE PRESENT INVENTION

The present invention overcomes the deficiencies of the prior art and provides a protecting and restraining apparatus for use in applying an intravenous system to an extremity, normally the arm, for substantially immobilizing the extremity while permitting continuous intravenous system operation. The present invention comprises an elongated, generally flat sheet member of a flexible material, the sheet member having a first cushioning surface of an absorbent material and a second cushioning surface of a material impervious to fluids, the sheet being adapted to be wrapped about and encompass the arm. The sheet member further comprises a main base portion and a plurality of first and second straps integrally formed with and transversely depending from the main base portion at opposing marginal longitudinal edges thereof, each set of straps being connected to adjacent straps at selective points along confronting marginal transverse edges of the adjacent strap to allow selective severance of the straps from each other. An elongated sleeve member is pivotally attached to the first or upper surface of the sheet member coextensively along a marginal longitudinal edge of the main base portion and the sleeve member to allow the sleeve member to pivot toward and away from the first surface of the sheet member, the sleeve member being adapted to accept and retain a stiffening member or board by being open at one end and closed at the other. A means for securing the sheet member and the sleeve member in engagement with a corresponding confronting portion of the arm, when the sheet member is wrapped about the arm, is further provided, the securing means including an exposed fastening means in the form of an adhesive strip, positioned selectively near the longitudinal marginal edge of the first surface of the first strap members for adhering to the second surface of a corresponding mating second strap member, thereby allowing selective tightening of the apparatus.

BRIEF DESCRIPTION OF THE DRAWINGS

For a further understanding of the nature and objects of the present invention, reference should be had to the following description taken in conjunction with the accompanying drawings in which like parts are given like reference numerals and, wherein.

DETAILED DESCRIPTION OF THE PREFERRED EMBODIMENT

Figure 1:
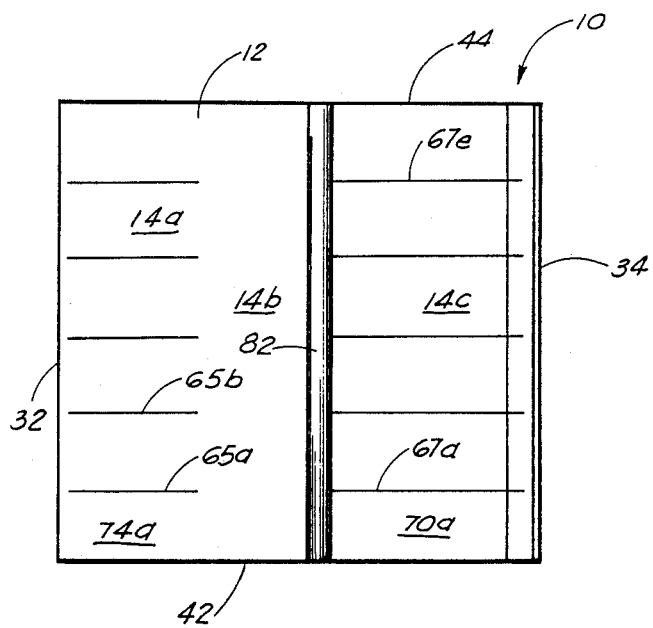
FIG. 1 is a top plan view of the preferred embodiment of the apparatus of the present invention.
Figure 2:
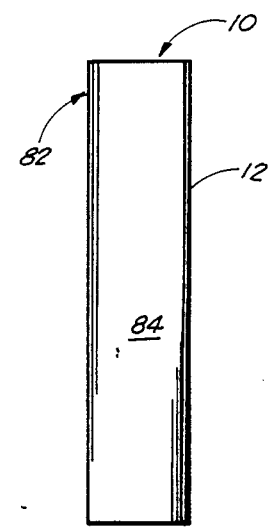
FIG. 2 is a right side elevational view of the embodiment of FIG. 1.
Figure 3:
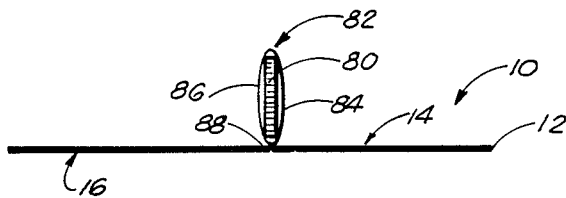
FIG. 3 is a front elevational view of the embodiment of FIG. 1.
Figure 4:
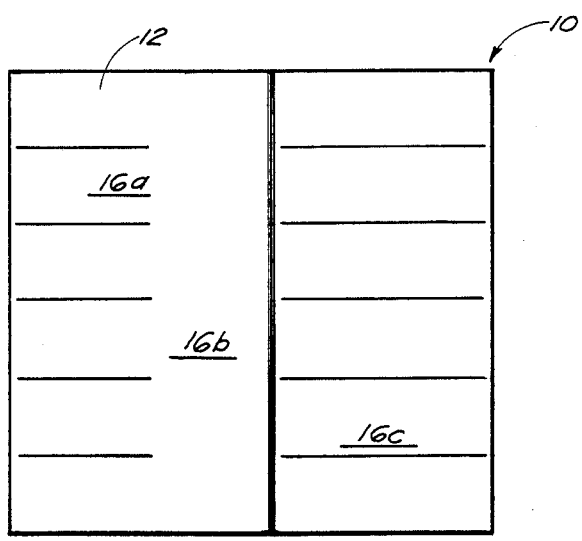
FIG. 4 is a bottom plan view of the embodiment of FIG. 1.
Figure 5:
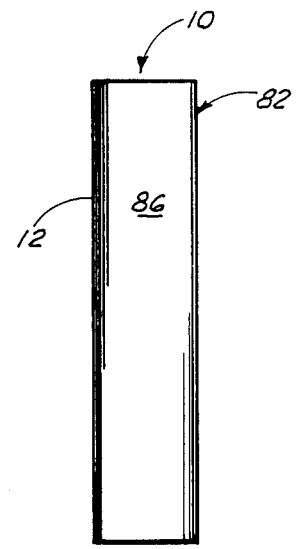
FIG. 5 is a left side elevational view of the embodiment of FIG. 1.
Figure 6:
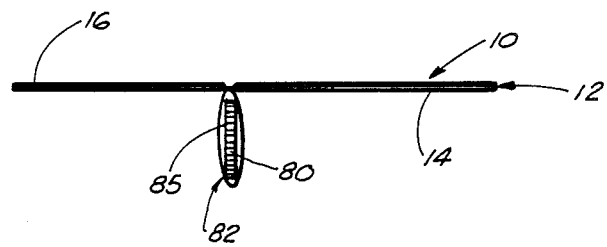
FIG. 6 is a rear elevational view of the embodiment of FIG. 1.
Figure 7:
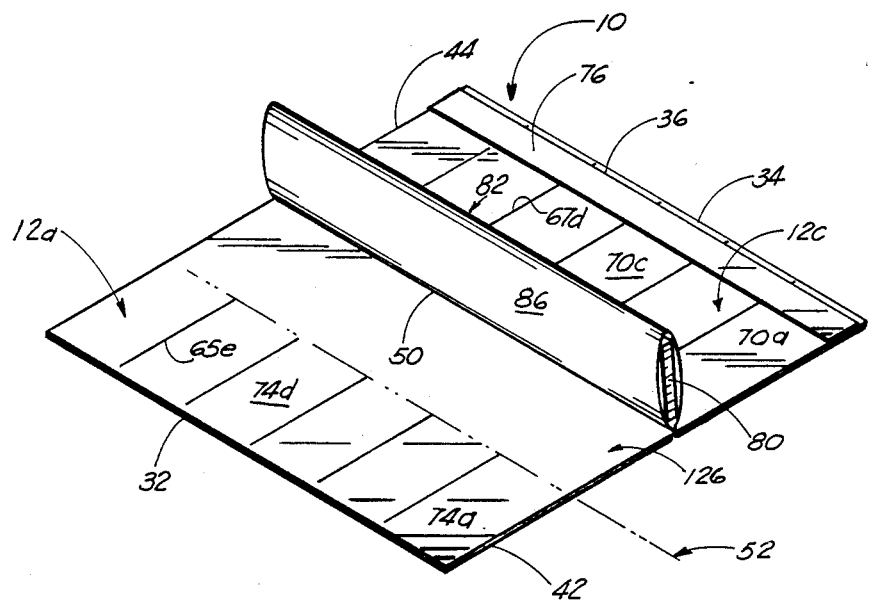
FIG. 7 is a top perspective view of the embodiment of FIG. 1.
Figure 8:
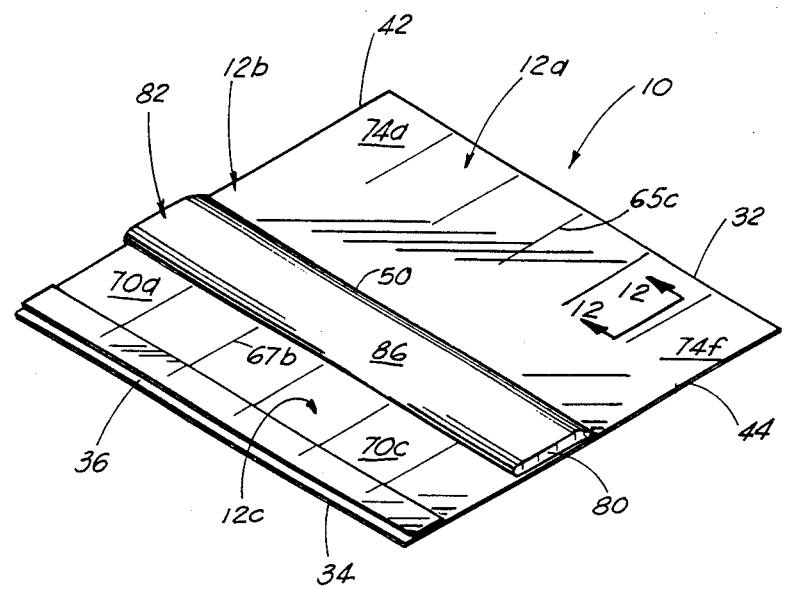
FIG. 8 is another top perspective view of the embodiment of FIG. 1.
Figure 9:
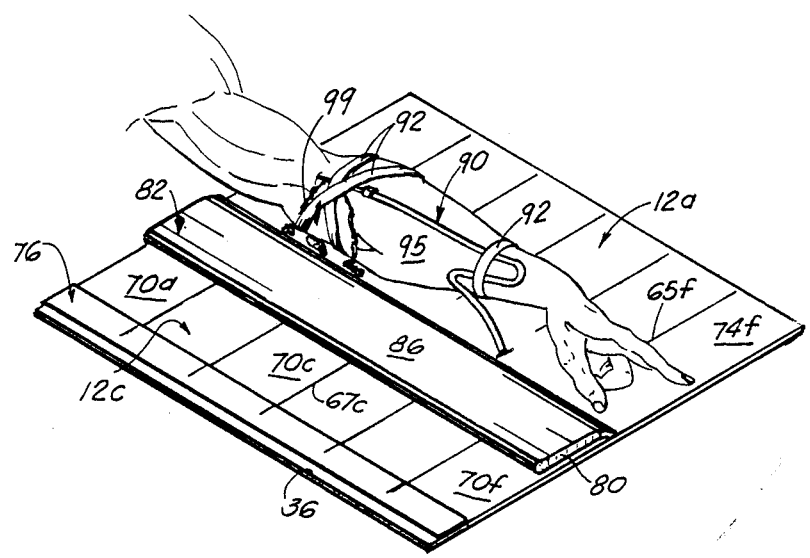
FIG. 9 is the top perspective view of FIG. 8 during the application of intravenous tubing to the arm of the patient.
Figure 10:
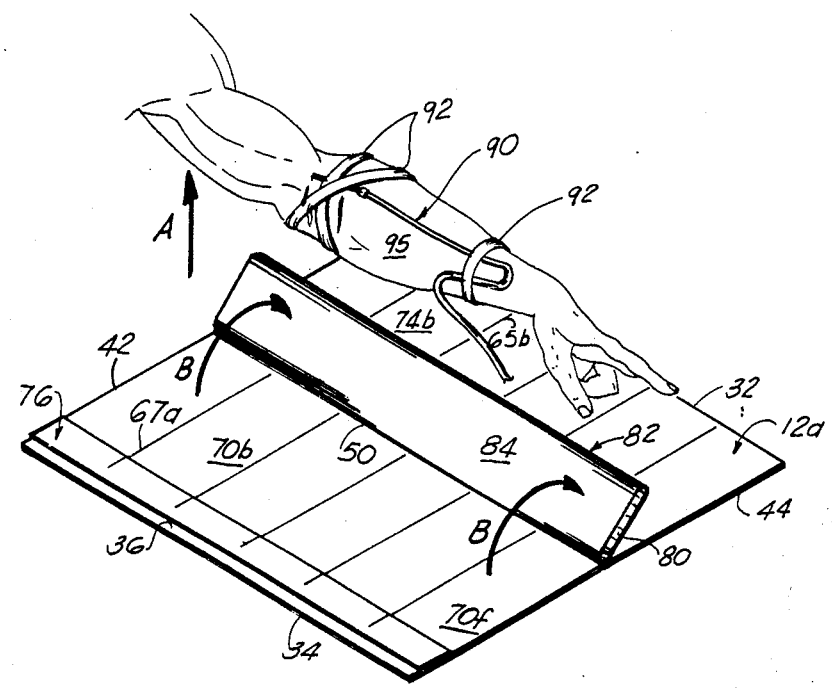
FIG. 10 is another top perspective view of the embodiment of FIG. 1, the view illustrating an intermediate stage of preparation for application of the apparatus to the patient's arm.
Figure 11:
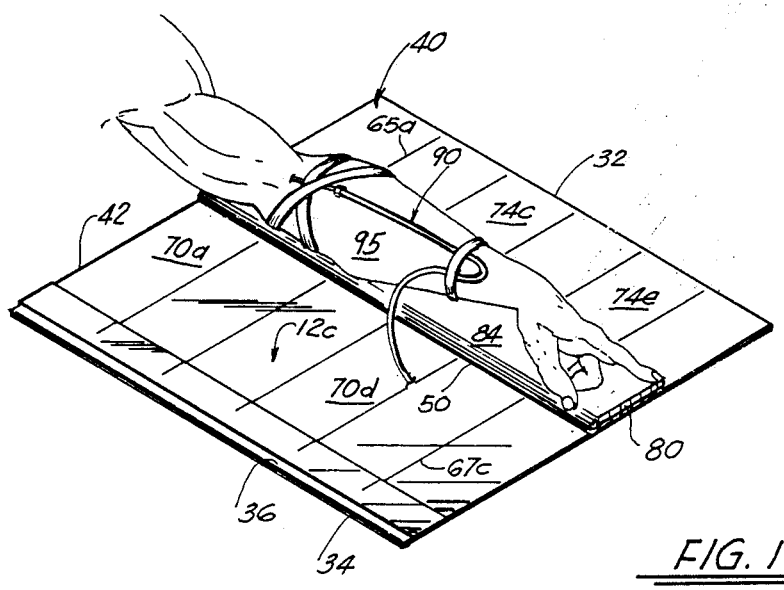
FIG. 11 is yet another top perspective view of the embodiment of FIG. 1 immediately prior to the securing of the apparatus to the patient's arm.

To best understand the apparatus of the present invention, the traditional apparatus for and method of immobilizing an extremity, such as the arm, while permitting the application of an intravenous or catheter system to an injured person is first discussed and best illustrated in FIGS. 18A-18E. This traditional method requires four (4) separate items: 4"×4" gauze pads 102, best shown in FIGS. 18A and 18B, an intravenous ("IV") arm board or splint 104, best shown in FIG. 18C, elastic banadaging or wrapping 106, best shown in FIG. 18D and tape 108, best shown in FIG. 18E (the tape is shown in its conventional container). After hurriedly reaching for all of these items at an emergency medical scene the paramedic places pads 102 under the patient's arm to absorb any blood that might flow when the IV is commenced. He then uses additional pads 102 to clean the arm of any further excess blood. He then lifts the arm and puts the IV board or splint 104 under the arm to keep the arm straight (there may be additional pads 102 between the board 104 and arm for cushioning) and then secures board 104 to the arm by wrapping about both the arm and board 104 the elastic bandaging 106 and finally securing the end of the bandaging 106 with tape from roll of tape 108. As aforestated, this traditional method is time consuming because it involves four separte items - pads 102, IV board or splint 104, elastic bandaging 106 and roll of tape 108.

The apparatus of the present invention is designated generally by the numeral 10. Apparatus 10 is best illustrated in FIGS. 1-8 and its application in FIGS. 9-11 and 14-17. Apparatus 10 (for simplicity entitled "Surgical Wrap With Arm Splint") is provided for use in applying an intravenous or catheter system to an extremity of the body, most commonly the arm, for protecting and substantially immobilizing or restraining the extremity, while permitting continued intravenous or catheter system operation. While the apparatus of the present invention can be applied to any extremity of the body, the description hereinafter will focus on the arm, the most common application. This focus of the arm should not be understood to in any way limit the claims provided hereinafter.

Figure 12:
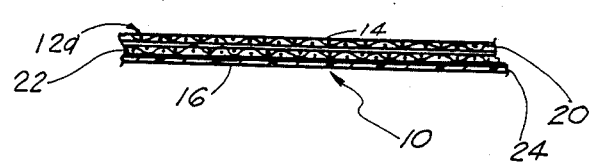
FIG. 12 is an enlargement of the crosssectional view taken along the Line 12—12 of FIG. 8.
Figure 13:
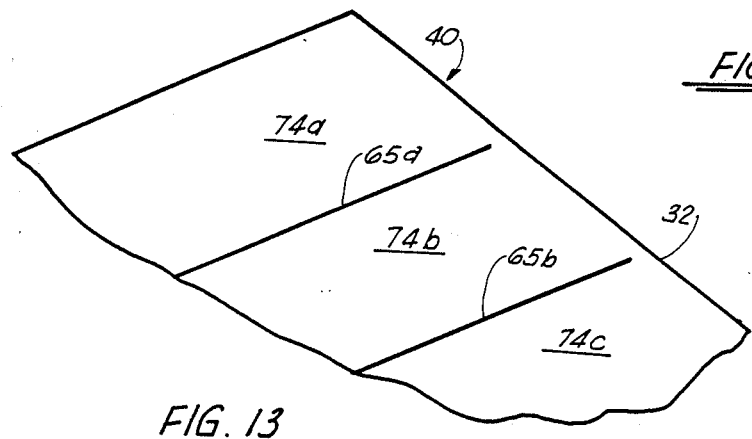
FIG. 13 is an enlarged partial top perspective view of the corner area (40) of FIG. 11.

Apparatus 10 comprises an elongated flexible sheet member 12, best seen in FIGS. 1, 4, 7 and 8. Elongated sheet member 12 is generally rectangular in shape (testing has shown 18"×26" to be the optimal size) and is of a flexible, pliable material. As best seen in FIG. 12, the preferred embodiment has a lower layer of polyethylene film 24 impervious to fluids, an upper layer of tissue ply 20 and an intermediate or middle layer 22 of the same tissue ply. Thus, sheet member 12 is two plies of tissue which are creped welded and then embossed by polyethylene film on the underside. In an alternate embodiment sheet member 12 may be spunbond (diaper liner) non-woven material adhesively bonded to plies of tissue.

Sheet member 12, as best seen in FIGS. 1, 4, 7 and 12, has a first surface area 14 of the aforementioned tissue ply material 20 and second surface 16 of the aforementioned polyethylene 24. Sheet member 12 is comprised of central or main base portion 12b and integrally transversely depending end or outer portions 12a, 12c. End portion 12a is integrally formed with central portion 12b and is further comprised of a plurality of strips or strap members 74a-74f divided by perforated or scored lines 65a-65e, as best seen in FIGS. 1, 4, 7-11 and 14, thus, straps 74a-74f are integrally formed with and transversely depend from one first marginal longitudinal edge 52 (best seen in FIG. 7) of main base portion 12b, each of straps 74a-74f being connected to its adjacent straps 74 at selective points along the confronting marginal transverse edges 77 (see 77a and 77b for illustration in FIGS. 14) of adjacent straps 74. Thus, strap 74b integrally transversely depends from main base portion 12b at the marginal longitudinal edge 52 of main base portion 12b, strap 74b being severably connected at its marginal edges 77b, 77b' (not shown) along scored or perforated lines 65a and 65b, respectively, to its adjacent straps 74a and 74c at their marginal edges 77a and 77c. In a fashion similar to end portion 12a, end portion 12c of sheet member 12 transversely, integrally depends from main base portion 12b and is divided into strips or strap members 70a-70f by perforated or scored lines 67a-67e, best seen in FIGS. 1, 4, 7-11 and 15-17. Thus straps 70a-70f are integrally formed with and transversely depend from main base portion 12b at the opposing marginal longitudinal edge 50 of main base portion 12b, each of straps 70a–70f being severably connected to its adjacent straps 70 at selective points along the confronting marginal transverse edge (not shown) of the adjacent straps 70. Thus, for example, straps 70c is integrally formed with main base portion 12b and transversely depends therefrom at the marginal longitudinal edge 50 of main base portion 14b, strap 70c being severably connected to adjacent straps 70b and 70d along perforated or scored lines 67b and 67c at their marginal edges.

As best seen in FIGS. 3, and 6–11, an elongated flexible sleeve member 82 is pivotally attached to sheet member 12. In the preferred embodiment, sleeve 82 is pivotally attached to sheet member 12 on the first or upper surface 14 thereof. Further, sleeve 82 is pivotally attached to sheet member 12 along marginal edge 88 of sleeve member 82 and marginal edge 50 of main base portion 12b of sheet member 12. In this manner, elongated sleeve member 82 is substantially coextensive with elongated sheet 12 and pivots, as seen by ARROWS B of FIG. 10, about interconnected marginal edges 50 of sheet 12 and 88 of sleeve 82. Sleeve 82, being of the same material as surface 14 of sheet member 12, that is absorbent tissue ply, is also flexible. Sleeve member 82 thus defines first and second curved surfaces 84, 86, best seen in FIGS. 2, 3 and 5–11, and central hollow core 85 for accepting through either open end a stiffening member 80 of a length substantially equal to the length of sleeve 82 and sheet member 12. Surfaces 84, 86 are of a width substantially equal to the width of main base portion 12b. Stiffening member 80 is therefore slightly not as wide as surfaces 84, 86 and may be of any material stiffer than flexible sheet member 12, although in the preferred embodiment, a cardboard member 80 is provided. Other stiffening member material may be wood, a lightweight metal such as aluminum, or the like. Sleeve member 82, may in an alternate embodiment, be closed at one end and open at the other to allow stiffener 80 to be inserted into core 85 and yet reduce the likelihood of it inadvertently sliding out of sleeve 82.

As best seen in FIGS. 7–11, sleeve 82 pivots about the longitudinal line defined by interconnected longitudinal marginal edges 50 of main base portion 12b and 88 of sleeve member 82. Sleeve member 82 pivots from a first position, best shown in FIG. 11, where it substantially covers main base portion 12b to the intermediate position of FIGS. 6 and 7 where it is substantially vertical and thus perpendicular to sheet member 12. From the substantially vertical position of FIGS. 6 and 7 it also pivots, as best illustrated by the opposite direction of ARROWS B in FIG. 10, to the position of FIG. 8 where it uncovers main base portion 12b and covers the interior area of end portion 12c.

Figure 14:
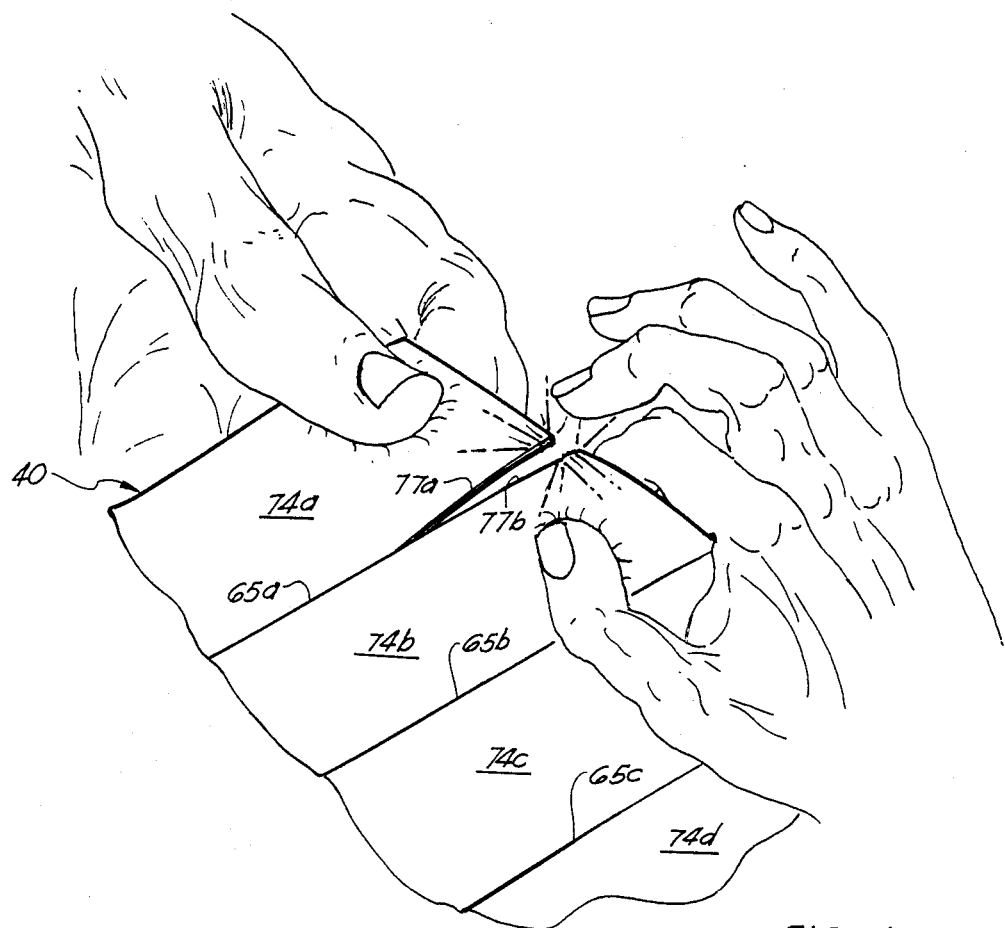
FIG. 14 is an enlarged partial view of the corner area (40) of the view of FIGS. 11 and 13 illustrating the separation of one of the scored or perforated strips of the sheet member of the preferred embodiment of the apparatus of the present invention.
Figure 18A:
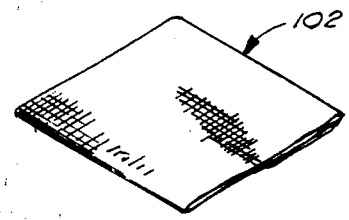
FIG. 18A is a top perspective view of a gauze pad of the prior art.
Figure 18B:
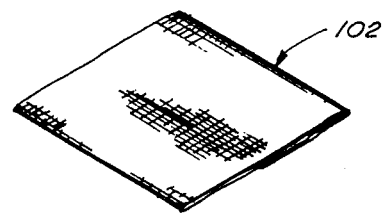
FIG. 18B is a top perspective view of another gauze pad required of the prior art.
Figure 18C:
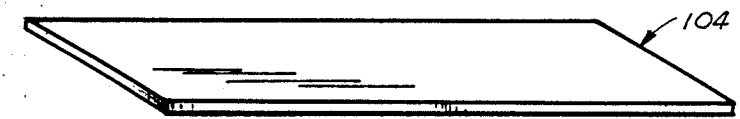
FIG. 18C is a top perspective view of an arm board or splint of the prior art.
Figure 18D:
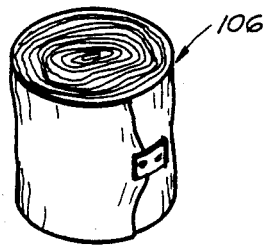
FIG. 18D is a top perspective view of a wrapping of the prior art.
Figure 18E:
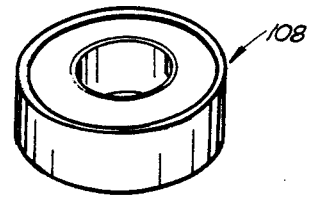
FIG. 18E is a top perspective view of a roll of tape and its container of the prior art.
Figure 15:
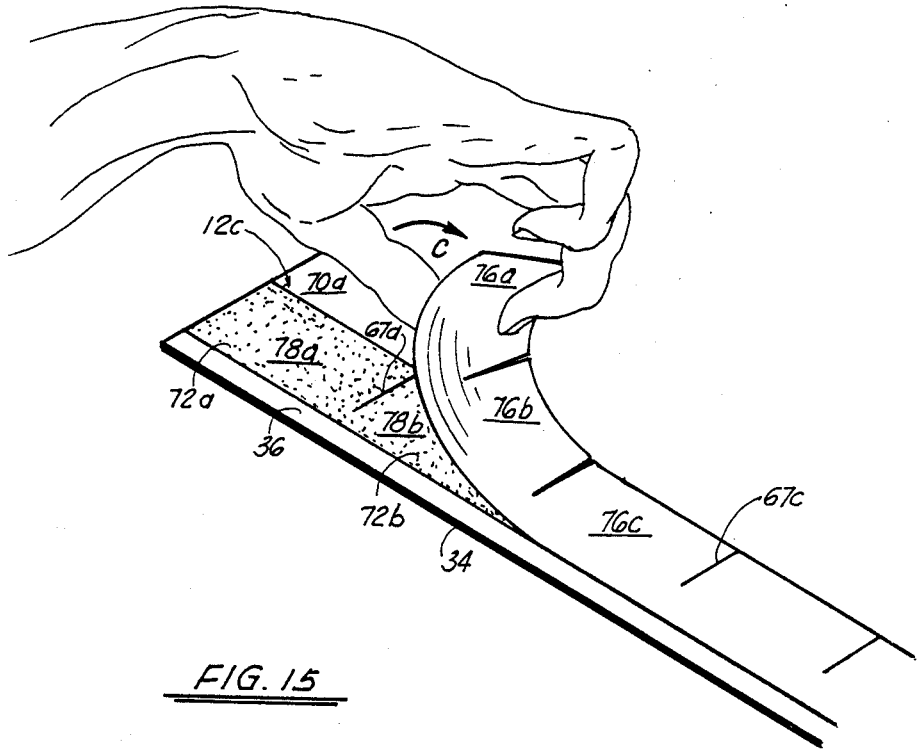
FIG. 15 is an enlarged partial top perspective view of one of the marginal longitudinal side edges of the sheet member of the preferred embodiment of the apparatus of the present invention with the adhesive portion being partially exposed.

As best seen in FIGS. 7–11 and 14–17, apparatus 10 is provided with a means for securing sheet member 12 and sleeve member 82 into engagement with a corresponding portion of arm 95 when sheet member 12 is wrapped about arm 95. The securing means comprises adhesive areas 78a–78f provided on upper surface 14 of end portion 12c at the marginal edges 72a–72f of each of straps 70a–70f. As best seen in FIG. 15, marginal edge 34 of sheet member 12 is folded over to provide unitary lip portion 36. Inwardly of lip portion 36 on surface 14 of sheet member 12 is provided a marginal longitudinal strip of adhesive 78 which can be divided into areas 78a–78f corresponding to straps 70a–70f. The adhesive can be protected until use, described hereinbelow, by non-adhesive strip 76 which can be selectively removed in the direction of ARROW C for application. It can thus be seen that lip 36 is of the same material 24 as second surface 16 of sheet member 12, but is easily severed along perforated or scored lines 65 as will be discussed further hereinbelow. Adhesive area 78 is of such composition that it can adhere to either of surfaces 14, 16 of sheet member 12 and allow selective tightening of apparatus 10 as it is applied, best shown in FIGS. 16 and 17, and to be discussed further hereinbelow.

The application of the apparatus 10 of the present invention can be best understood from FIGS. 8–11 and 13–7. First, the apparatus of the present invention 10 is laid out flat with surface 14 being the upper surface, surface 16 being the lower or under surface and sleeve 82 pivoted to the position of FIG. 8 so that main base portion 12b of sheet member 12 and surface 86 of sleeve member 82 are exposed and surface 84 of sleeve member 82 covers the interior area of end portion 12c of sheet member 12. Now the arm 95 of the patient can be placed longitudinally upon surface area 14b of main base portion 12b (for purposes of this application, the arm 95 is placed longitudinally from edge 42 of sheet member 12 to edge 44, this being the direction from the upper arm to the forearm). Now intravenous line (IV line) or catheter system 90 is inserted into the patient and secured to arm 95 by fasteners or straps 92. The natural consequence of such intravenous or catheter insertion is to produce blood 99 which consequently flows down the arm 95 dripping onto main base portion 12b of sheet member 12 where arm 95 has been placed. It can also be expected that some blood 99 will also descend upon side 86 of sleeve member 82 (remember sleeve member 82 is also made of the soft flexible pliable material 20 of the upper surface of sheet member 14). Thus, it can be understood that surface or side 86 of sleeve member 82 and first surface 14b of main base portion 12b will absorb the blood 99 dripping from arm 95. Once the arm 95 is cleansed of blood 99 remaining thereon, the arm is lifted off of or away from apparatus 10 (in the direction of ARROWS A in FIG. 10) and sleeve 82 is pivoted, in the direction of ARROWS B, also best shown in FIG. 10, until it reaches the position of FIG. 11 where the bloodied side 86 of sleeve 82 now engages bloodied main base portion 12b of sheet 12. Now only the clean, soft surface area of area 84 of sleeve 82 and surface areas 12a, 12c of sheet member 12 are exposed to arm 95 still containing intravenous or catheter system 90. Now apparatus 10 is poised to be fully applied to arm 95 to protect and restrain it and permit continued intravenous or catheter system operation.

As best seen in FIG. 14, flexible second strip or strap members 74a–74f are selectively severed from each other along perforated or scored lines 65a–65 e. This is accomplished, as best seen in FIG. 14, by manually grasping any two adjacent straps 74 (here straps 74a and 74b) near the marginal edge 32 where they are connected and pulling them apart all the way down the perforated or scored line 65 (here line 65a).

Once the straps 74a–74f separated from each other, attention is turned to the other set of flexible straps 70a–70f. However, before separating straps 70a–70f along perforated or scored lines 67, adhesive covering strip 76 is pulled upwardly in the direction of ARROW C in FIG. 15 to expose adhesively coated edges 72a–72f of straps 70a–70f, respectively, positioned along marginal edge 34 of sheet member 12 (although in an alternate method of operation, straps 70a–70f can be separated along scored lines 67a–67e and still be covered with strip 76 (which is now in smaller portions 76a–76f) and these smaller strips 76a–76f can be individually removed). Now straps 70a–70f are separated as described hereinabove with respect to straps 74a–74f. With straps 70a–70f and 74a–74f free from their formerly adjacently connected strap members, a paramedic applying apparatus 10 can begin securing it about arm 95.

Figure 16:
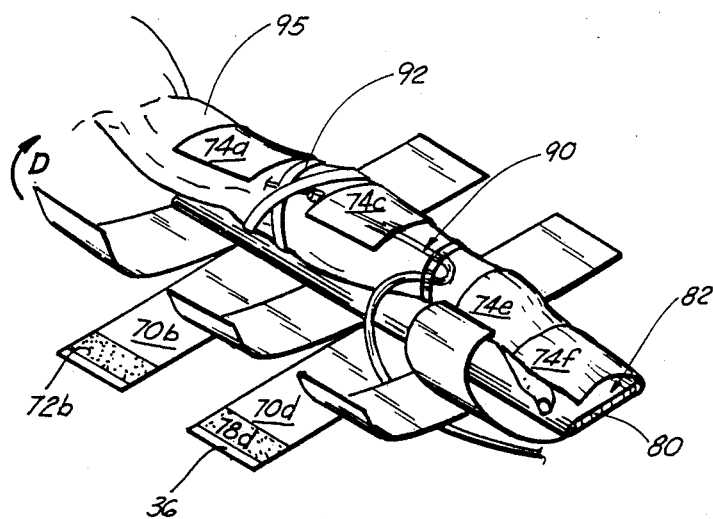
FIG. 16 is a top perspective view of the embodimemt of FIG. 11 illustrating an intermediate stage of securing the apparatus to the patient's arm.
Figure 17:
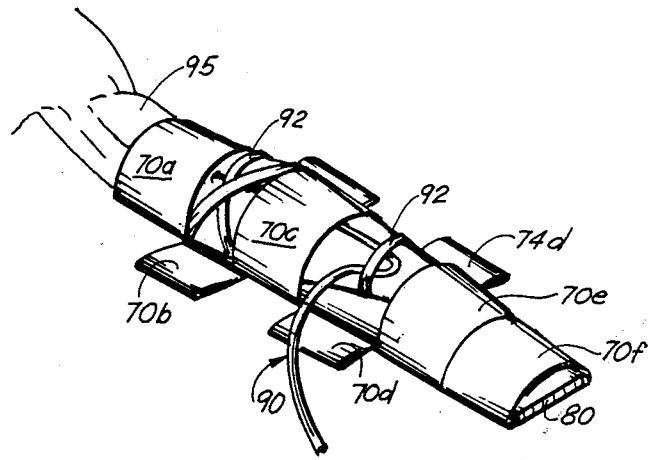
FIG. 17 is a top perspective view of the embodiment of FIG. 11 illustrating one method of final application of the apparatus to the patient's arm.

The paramedic may first choose any of straps 74 and wrap it over arm 95, as best seen in FIG. 16. For example, first strap 74a can be laid across arm 95 and then straps 74c, 74e and 74f in turn which is the situation illustrated in FIG. 16. Then strap 70a can be lifted in the direction of ARROW D until adhesive area 78a on edge 72a overlaps and contacts surface 16 of strap 74a and securely fastens strap 70a to strap 74a. This same procedure is followed with other pairs of mating straps 70c–74c, 70e–74e and 70f–74f until apparatus 10 is secured to arm 95. As best seen in FIG. 17, strap 70a–74a, 70c–74c, 70e–74e and 70f–74f have been respectively secured to each other to fasten apparatus 10 to arm 95, yet leave exposed portions of the IV system 90 and fasteners 92. Even though strap pairs 70b, 74b and 70d, 74d are not used to wrap arm 95 but to expose IV system 90 to view, they can be conveniently tucked out of the way by rolling marginal edge of strap 70b over onto itself so that adhesive portion 78b contacts surface 14a and is tucked under arm 95 and strap 74b is rolled over onto itself and tucked under arm 95 (even though there is no adhesive on strap 74b it will still remain nicely tucked under the arm). Thus the application of FIG. 17 is accomplished. Of course, in a different application the entire arm can be covered with straps 70–74, or other combinations employed to expose portions of the IV and catheter system 90.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A protecting and restraining apparatus for use in applying an intravenous or catheter system to an extremity of the body for substantially immobilizing the extremity while permitting continuous intravenous catheter system operation comprising:
   (a) an elongated flexible sheet member being adapted to be wrapped about and encompass an extremity of the body, said sheet member further comprising:
   i. a main base portion; and,
   ii. a plurality of strap members integrally formed with and transversely depending from said main base portion at a marginal longitudinal edge of said main base portion, each of said strap members being severably connected to its adjacent strap members at selected points along confronting marginal transverse edges of said adjacent strap members;
   (b) an elongated flexible sleeve member pivotally attached to said sheet member along one marginal longitudinal edge of said sleeve member so as to allow pivoting of said sleeve member toward and away from a first surface of said sheet member, said sheet member being adapted to accept and retain a stiffening member therein; and,
   (c) means for securing said sheet member and said sleeve member in engagement with a corresponding confronting portion of said extremity when said sheet member is wrapped about said extremity.

2. The apparatus of claim 1, wherein said sheet member is of a generally rectangular configuration.

3. The apparatus of claim 1, wherein said sheet member has a first surface of a cushioning absorbent material.

4. The apparatus of claim 1, wherein said sheet member has a second surface of a material impervious to fluids.

5. The apparatus of claim 1, wherein said sheet member further comprises a plurality of second strap members integrally formed with and transversely depending from said main base portion at the opposing marginal longitudinally edge of said main base portion, each of said second strap members being connected to its adjacent second strap members at selective points along confronting marginal transverse edges of said adjacent second strap members.

6. The apparatus of claim 1, wherein said sleeve member is open at one end and closed at the other for accepting and retaining said stiffening member.

7. The apparatus of claim 1, wherein said securing means includes fastening means positioned selectively near the longitudinal marginal edge of said strap members for adhereing to the opposing surface of said sheet member, thereby allowing selective tightening of said apparatus.

8. A protecting and restraining apparatus for use in applying an intravenous or catheter system to an extremity of the body for substantially immobilizing the extremity while permitting continued intravenous or catheter system operation comprising:
   (a) an elongated flexible sheet member, said sheet member being adapted to be wrapped about an encompass an extremity of the body, said sheet member further comprising:
   i. a main base portion; and,
   ii. a plurality of strap members integrally formed with and transversely depending from said main base portion at a marginal longitudinal edge of said main base portion, each of said strap members being severably connected to its adjacent strap members at selective points along confronting marginal transverse edges of said adjacent strap members;
   (b) an elongated flexible sleeve member pivotally attached to said sheet member along one marginal edge of said sleeve member so as to allow pivoting of said sleeve member toward and away from a first surface of said sheet member, said sleeve member being adapted to accept and retain a stiffening member therein; and,
   (c) means for securing said sheet member and said sleeve member in engagement with a corresponding confronting portion of said extremity when said sheet member is wrapped about said extremity.

9. The apparatus of claim 8, wherein said sheet member is of a generally rectangular configuration.

10. The apparatus of claim 8, wherein said sheet member has a first cushioning surface of an absorbent material and a second surface of a material impervious to fluids.

11. The apparatus of claim 8, wherein said sheet member further comprises a plurality of second strap members integrally formed with and transversely depending from said main base portion at the opposing marginal longitudinal edge of said main base portion, each of said second strap members being connected to its adjacent second straps at selective points along confronting marginal transverse edges of said adjacent second strap members.

12. The apparatus of claim 8, wherein said sleeve member is attached to a first surface of said sheet member coextensively along one marginal longitudinally edge of said main base portion and said sleeve member, so as to allow pivoting of said sleeve member toward and away from said first surface of said sheet member.

13. The apparatus of claim 12, wherein said sleeve member is open at one end and closed at the other for accepting and retaining said stiffening member.

14. The apparatus of claim 8, wherein said securing means includes exposed fastening means positioned selectively near the longitudinal marginal edge of a first surface of said strap members for adhering to the opposing surface of said sheet member, thereby allowing selective tightening of said apparatus.

15. The apparatus of claim 8, wherein said sleeve member is pivotally affixed to said first surface of said main base portion by stitching along the longitudinal marginal edge of said sleeve member.

16. A protecting and restraining apparatus for use in applying an intravenous or catheter system to an extremity of the body for substantially immobilizing the extremity while permitting continued intravenous or catheter system operation comprising:
(a) an elongated flexible sheet member, said sheet member having a first cushioning surface and a second coated surface, said sheet member being adapted to be wrapped about and encompass an extremity of the body, said sheet member further comprising:
i. a main base portion; and,
ii. a plurality of strap members integrally formed with and transversely depending from said main base portion at a marginal longitudinal edge of said main base portion, each of said strap members being severably connected to its adjacent strap members at selective points along confronting marginal transverse edges of said adjacent strap members;
(b) an elongated flexible sleeve member being pivotally attached to said sheet member along one marginal edge of said sleeve member, so as to allow pivoting of said sleeve member toward and away from said first surface of said sheet member, said sleeve member being adapted to accept and retain a stiffening member therein; and,
(c) means for securing said sheet member and said sleeve member in engagement with a corresponding confronting portion of said extremity when said sheet member is wrapped about the extremity, said securing means including exposed fastening means positioned selectively on said strap members for adhering to said sheet member, thereby allowing selective tightening of said apparatus.

17. The apparatus of claim 16, wherein said sheet member is of a generally rectangular configuration.

18. The apparatus of claim 16, wherein said sheet member further comprises a plurality of second strap members integrally formed with and transversely depending from said main base portion at the opposite marginal longitudinal edge of said main base portion, each of said second strap members being connected to its adjacent second strap members at selective points along confronting marginal transverse edges of said adjacent second strap members.

19. The apparatus of claim 16, wherein said sleeve member is open at one end and closed at the other for accepting and retaining said stiffening member.

20. The apparatus of claim 16, wherein said fastening means is exposed selectively near the longitudinal marginal edge of the first surface of said first strap members for adhering to said second surface of said sheet member, thereby allowing selective tightening of said apparatus.

21. A protecting and restraining apparatus for use in applying an intravenous or catheter system to an extremity of the body for substantially immobilizing the extremity while permitting continued intravenous or catheter system operation comprising:
(a) an elongated, flat, flexible sheet member, said sheet member having a first cushioning surface of an absorbent material and a second surface of a material impervious to fluids, said sheet member being adapted to be wrapped about and encompass an extremity of the body, said sheet member further comprising:
i. a main base portion;
ii. a plurality of first strap members integrally formed with and transversely depending from said main base portion at a first marginal longitudinal edge of said main base portion, each of said first strap members being connected to its adjacent first strap members at selective points along confronting marginal transverse edges of said adjacent first strap members; and,
iii. a plurality of second strap members integrally formed with and transversely depending from said main base portion at the opposite marginal longitudinal edge of said main base portion, each of said second strap members being connected to its adjacent second strap members at selective points along confronting marginal transverse edges of said adjacent second strap members;
(b) an elongated flexible sleeve member being pivotally attached to said first surface of said sheet member coextensively along one marginal edge of said main base portion and said sleeve member, so as to allow pivoting of said sleeve member toward and away from said first surface of said sheet member, said sleeve member being adapted to accept and retain a stiffening member by being open at one end and closed at the other; and,
(c) means for securing said sheet member and said sleeve member in engagement with a corresponding confronting portion of said extremity when said sheet member is wrapped about said extremity, said securing means including exposed fastening means positioned selectively near the longitudinal marginal edge of the first surface of said first strap members for adhering to said second surface of said second strap members, thereby allowing selective tightening of said apparatus.

* * * * *